United States Patent [19]

Klaveness et al.

[11] Patent Number: 5,416,223
[45] Date of Patent: May 16, 1995

[54] IODINATED ESTERS

[75] Inventors: Jo Klaveness; Per Strande, both of Oslo, Norway

[73] Assignee: Nycomed Imaging AS, Oslo, Norway

[21] Appl. No.: 315,502

[22] Filed: Sep. 30, 1994

Related U.S. Application Data

[60] Division of Ser. No. 210,739, Mar. 21, 1994, Pat. No. 5,370,861, which is a continuation of Ser. No. 688,488, May 20, 1991, abandoned.

[30] Foreign Application Priority Data

Jan. 9, 1989 [GB] United Kingdom ................ 8900376

[51] Int. Cl.$^6$ .................... C07C 69/78; C07D 317/34; C07D 333/32
[52] U.S. Cl. ......................... 549/65; 549/229; 549/448; 549/479; 546/302; 558/270; 558/275; 558/276
[58] Field of Search .......................... 558/270, 275, 276; 549/65, 229, 448

[56] References Cited

U.S. PATENT DOCUMENTS

| | | | |
|---|---|---|---|
| 3,795,698 | 3/1974 | Soulal et al. | 558/270 |
| 4,018,783 | 4/1977 | Soulal et al. | 558/270 |
| 4,440,692 | 4/1984 | Kalbacher et al. | 558/270 |

FOREIGN PATENT DOCUMENTS 866184 4/1961 United Kingdom .
2157283 10/1985 United Kingdom .

OTHER PUBLICATIONS

Chemical Abstracts Registry Handbook (1965–1971) registry Nos. 12700–00–0 through 17799–99–4, p. 5556R.
Wiegert, Chemical Abstracts, vol. 84 (1976) No. 84: 89851h.
Tilly, Chemical Abstracts, vol. 84 (1976) No. 184,889k.

Primary Examiner—Robert W. Ramsuer
Attorney, Agent, or Firm—Bacon & Thomas

[57] ABSTRACT

Water insoluble iodinated esters of formula (I), in which $R^1$ is a substituted or unsubstituted $C_{1-20}$ aliphatic, $C_{7-20}$ araliphatic or $C_{6-20}$ aryl group or a $C_{1-20}$ heterocyclic group having one or more hereto atoms selected from O, S and N; $R^2$ is hydrogen or a substituted or unsubstituted $C_{1-6}$ aliphatic, $C_{6-10}$ aryl or $C_{7-20}$ araliphatic group; and $R^3$ is a group as defined above for $R^1$, which may be the same as or different from $R^1$, or $R^2$ and $R^3$ together represent a substituted or unsubstituted $C_{1-4}$ alkylene group, the molecule containing at least one iodine atom and being metabolisable to products which are soluble in body fluids and are physiologically acceptable. The esters are useful in X-ray and ultrasound imaging, especially liver and spleen imaging.

5 Claims, No Drawings

IODINATED ESTERS

This application is a Division of application Ser. No. 08/210,739, filed Mar. 21, 1994, now U.S. No. 5,370,861, which is a Continuation of application Ser. No. 07/688,488, filed May 20, 1991, now abandoned.

The present invention relates to contrast agents for medical X-ray and ultrasound imaging, and to their preparation and use.

It has been proposed to improve the detection of lesions in the liver and spleen by the use of contrast agents which accumulate in these organs. A number of substances have been suggested but there is no such product on the market at the present time and each of the contrast agents so far proposed has some disadvantages.

Since the reticuloendothelial system of the liver and spleen is well known to trap particles by phagocytosis, contrast agents in particulate form are particularly well adapted for visualisation of these organs. Emulsions of iodinated oils have been proposed in this context, particularly iodinated ethyl esters of poppy seed oil. (Vermess, M., et al, Radiology, 137 (1980) 217). However, these substances have proved unduly toxic.

Another possibility is to use liposomes containing water soluble iodinated contrast agents. (Havron A. et al, Radiology, 140 (1981) 507). However, since only a limited amount of iodine can be incorporated in each liposome, it is necessary to administer relatively large amounts of lipids in order to attain adequate contrast enhancement. This tends to cause emboli in the lung capillaries. Furthermore, liposomes have been found to be relatively unstable on storing (Shulkin, P. M., et al, J. Microencapsul., 1 (1984) 73).

Submicron thorium dioxide particles have been used for liver visualisation and have shown effective enhancement of contrast in clinical testing but their use has been discontinued because of the extremely lengthy retention of the particles in the liver. This, in combination with the inherent radioactivity of thorium, has led to serious adverse side effects, including neoplasm and fibrosis. (Thomas, S. F., Radiology, 78 (1962) 435).

It has also been proposed to use particles comprising the ethyl ester of the water soluble X-ray contrast agent, iodipamide (Violante, M. R., et al, Invest. Radiol., 2, (1984) 133). However, ethyl esters are not sufficiently metabolically labile and thus would be expected to be retained in the liver for a considerable period. Indeed, both this ester and an iodinated ethyl ester of poppy seed oil gave an increase in lipid vacuoles in the hepatocytes after intravenous administration. (Vetmess et al, Radiology, 137 (1980) 217) and Violante M. R., Invest. Radiol., 2 (1984) 133). Such morphological changes indicate an adverse effect on the hepatocytes.

Acyloxyalkyl esters of carboxylic acids containing a tri-iodophenyl group are known as contrast agents from GB-A-1363847, U.S. Pat. No. 4,018,783 and GB-A-157283. In U.S. Pat. No. 4,018,783 the compounds are primarily suggested for X-ray imaging of the bronchial system, while in GB-A-2157283 the most preferred use is in a liposome carrier in lymphography.

We have now found that particularly advantageous contrast agents for the visualisation of the liver and spleen comprise particulate lipophilic iodine-containing carbonate esters which are metabolically labile to form water-soluble substances which are substantially non-toxic and are not retained in the target organs.

According to the present invention we provide metabolically labile water-insoluble iodinated esters of the formula (I):

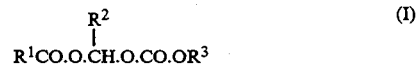

$$R^1CO.O.\overset{R^2}{\underset{|}{CH}}.O.CO.OR^3 \qquad (I)$$

in which $R^1$ is a substituted or unsubstituted $C_{1-20}$ aliphatic, $C_{7-20}$-araliphatic or $C_{6-20}$ aryl group or a $C_{1-20}$ heterocyclic group having one or more hetero atoms selected from O, S and N;

$R^2$ is hydrogen or a substituted or unsubstituted $C_{1-6}$ aliphatic group, $C_{6-10}$ aryl group or $C_{7-20}$ araliphatic group;

$R^3$ is a group as defined above for $R^1$, which may be the same as or different from $R^1$, or $R^2$ and $R^3$ and together represent a substituted or unsubstituted $C_{1-4}$ alkylene group, the molecule containing at least one iodine atom and being metabolisable to products which are soluble in body fluids and are physiologically acceptable.

Where the group $R^3$ is not joined to $R^2$, the metabolic products will be $R^1COOH$, $R^2CHO$, $R^3OH$ and carbon dioxide. Where $R^3$ and $R^2$ together form an alkylene group, the products will be $R^1COOH$ and $HO(R^3.R^2)$-CHO and carbon dioxide.

Aliphatic groups may be straight or branched, saturated or unsaturated and include, for example, alkyl and alkenyl groups e.g. methyl, ethyl, isopropyl, butyl or allyl groups. Araliphatic groups include monocarbocyclic aryl-alkyl groups; for example benzyl groups. Aryl groups include mono- or bi-cyclic aryl groups, for example phenyl, tolyl or naphthyl groups. Heterocyclic groups include 5 or 6-membered heterocyclic groups preferably having one heteroatom, for example furyl, thienyl or pyridyl groups.

Possible substituents in the above hydrocarbon groups $R^1$, $R^2$ and $R^3$ include hydroxyl, etherified hydroxyl, esterified hydroxyl, etherified thiol, N-alkylamino, N—$C_{1-6}$-acylamino, N—$C_{1-6}$-acyl-N—$C_{1-6}$alkylamino, carbamoyl and N—$C_{1-6}$alkylcarbamoyl groups and halogen atoms. It should be noted that aromatic rings such as phenyl may carry $C_{1-6}$ alkyl groups, as in the tolyl group. Substituents may be present in combination and thus, for example, N-acyl and N-alkyl groups may carry hydroxy or etherified or esterified hydroxyl groups.

Etherified hydroxyl groups include $C_{1-5}$ alkoxy groups such as methoxy groups. Adjacent hydroxy groups may be etherified with a single bridging group, such as an acetonide group. Esterified hydroxyl groups include $C_{1-6}$ acyloxy groups such as acetoxy groups.

Halogen atoms include fluorine, chlorine, bromine and iodine. More than one halogen atom may be present in any particular group, as in the trifluoromethyl group. It is particularly preferred that the molecule as a whole carries several iodine atoms, for example at least three.

It is particularly preferred that at least one of the groups $R^1$ and $R^3$ contains an iodinated phenyl group, preferably a triiodophenyl group. Such a group may be selected from the very wide range of such groups present in commercial carboxylic acid or non-ionic amide X-ray contrast agents. Such groups include 2,4,6-triiodophenyl groups having at the 3- and/or 5-positions groups selected from carbamoyl, N-alkylcarbamoyl or N-hydroxyalkylcarbamoyl, acylamino, N-alkylacylamino and acylaminomethyl groups. In such groupings, acyl groups will commonly be acetyl groups and N-alkylacylamino groups will commonly be N-methylacetamino groups. N-hydroxyalkylcarbamoyl groups will commonly comprise 1,3 or 2,3-dihydroxypropyl groups as the hydroxyalkyl moiety. In the group $R^1$ the triiodophenyl group will preferably be linked directly to a carbonyl group, i.e. the compound of formula (I) will be an ester of a triiodobenzoic acid derivative, for example an X-ray contrast acid such as metrizoic acid, diatrizoic acid, iothalamic acid and ioxaglic acid. In the group $R^3$, however the triiodophenyl group may be linked directly to the oxygen atom (the compound then contains a substituted triiodophenoxy group) or via a bridging group as in the hydroxyalkylamino, N-hydroxyalkylcarbamoyl or hydroxyacylamino groups present in such non-ionic X-ray contrast agents as iohexol, iopentol, iopamidol, iopromide and metrizamide. Where such non-ionic contrast agents have multiple hydroxyl groups, the group $R^1CO.O.CHR^2.O.CO.O—$ may be attached at more than one position in the group $R^3$.

It is important that the contrast agent according to the invention is substantially water-insoluble and thus, when administered in particulate form, will be entrapped by the liver or spleen. It is possible for relatively hydrophilic groups, such as hydroxyl, to be present provided the remainder of the molecule is sufficiently lipophilic to ensure minimal overall water-solubility. However, after metabolic enzymolysis, it is important that the metabolic products have sufficient water-solubility at physiological pH to be excreted from the target organs. They should also themselves be physiologically acceptable.

We have found that particulate compounds according to the invention on intravenous administration appear to be captured by the reticuloendothelial system of the liver and spleen, the resulting accumulation of particles greatly assisting the imaging of these organs. On the other hand, the phagocytosing cells of the liver (Kupffer cells) contain lysosomes which possess a broad spectrum of hydrolytic enzymes including a number of esterases. Thus, once the particles are phagocytised, they enter the lysosomes and are converted into water-soluble products which are subsequently excreted. The relative rapidity of the conversion of the compounds into water-soluble products significantly decreases the risk of toxic reactions.

As compared with liposomes, the particles of solid contrast agent according to the invention have a very much higher iodine content. Thus, to achieve a desired level of contrast, as provided by a particular amount of iodine, a far smaller amount of material has to be used and the risk of producing lung emboli is greatly reduced. Furthermore, the particulate material according to the invention, which is commonly crystalline, is generally much more stable to storage than the previously proposed liposomes.

The compounds of the invention, due to their iodine content, provide excellent X-ray image enhancement. Due to the presence of the relatively heavy iodine atoms, the particles reflect ultrasound and can also be used in enhancement of ultrasound images.

The particulate compounds according to the invention are rapidly accumulated in the liver and spleen and are then retained in the organs, allowing imaging to take place on a more convenient timescale than with known non-ionic contrast agents where any retention in the liver is transient.

Thus when maximum liver-iodine concentration is reached, a concentration "plateau" is achieved which allows imaging to be carried out over a long period. When the elimination of the contrast agent from the liver begins, it proceeds very quickly so that the contrast agent is eliminated from the body after a short period.

This profile of liver uptake and excretion is particularly beneficial and represents a significant advantage over the prior art.

The particulate compounds of the invention also have low toxicity, for example about 4 times lower than the toxicity of corresponding particulate ester derivatives in which $R^3O.CO$ is replaced by $R^3CO$.

The invention also provides injectable contrast media comprising a compound according to the invention in particulate form in suspension in a liquid for injection.

The mean particle size of the contrast agent will, in general, be within the range 0.002 to 7 microns, preferably 0.01 to 3 microns.

The injectable liquid may be any sterile physiologically acceptable liquid such as physiological saline which may usefully contain a physiologically acceptable stabilising agent such as bovine serum albumen, human serum albumin, propylene glycol, gelatin, polyvinylpyrrolidone (for example having a molecular weight about 30,000 daltons), or a polysorbate (for example Polysorbate 80) or combinations of two or more of these stabilising agents.

The contrast media may be used in the enhancement of X-ray and ultrasound images of the liver and/or spleen of a human or non-human animal subject, in which method they will be administered intravascularly, normally intravenously, prior to imaging.

The compounds according to the invention may be prepared in any convenient way. In general, the compounds will be formed by esterification of an acid of the formula $R^1COOH$ or a functional derivative thereof with a compound of the formula $X—CHR^2.O.CO.OR^3$, where X is a leaving group such as a halogen atom or a mesyloxy or tosyloxy group. Where X represents a leaving group, the functional derivative of the acid of formula $R^1COOH$ will normally be a salt such as the potassium salt. Such a reaction will normally be carried out in solution, for example in a polar solvent such as dimethylformamide.

The compound $X—CHR^2O.CO.OR^3$ where X is halogen may in turn be prepared from $R^2CHO$ and a compound of formula $X^1.CO.OR^3$ wherein $X^1$ is halogen atom in the presence of a base such as pyridine.

The intermediates $X—CHR^2.O.C.OR^3$ may also be made by coupling a compound of formula $X—CHR^2—O.CO.Hal$ with an alcohol of formula $R^3OH$, Hal being a halogen atom. Where the group $R^3$ contains multiple hydroxyl groups as in iohexol, it may be desirable to protect certain of these with, for example, acetonide groupings, in order to ensure reaction at a single hydroxyl group. Such acetonide groups may if desired remain in the final compound according to the invention.

The particulate form of the contrast agent according to the invention may advantageously be prepared by precipitation from solution in a water-miscible solvent such as ethanol by admixture with water, which may conveniently contain a stabilising agent such as bovine serum albumin, human serum albumin, gelatin, polyvinylpyrrolidone, propylene glycol or a polysorbate, with vigorous agitation, e.g. using ultrasound. In this way, it is possible to obtain particles of mean diameter of the order of 1.0 microns. Mechanical crushing or spray drying, for example to an appropriate particle size is also suitable. The particles may be dispersed in the liquid for injection referred to above.

The following Examples are given by way of illustration only. Seronorm is a test serum available from Nycomed AS, Oslo, Norway.

EXAMPLE 1

1-(Ethyloxycarbonyloxy) ethyl 5-(N-acetylamino)-3-(N-acetyl-N-methylamino)-2,4,6-triiodobenzenecarboxylate 1-Chloroethyl ethyl carbonate (10.00 g, 66.0 mmol) was added dropwise during 1.5 hour at room temperature to a solution of potassium 5-(N-acetylamino)3-(N-acetyl-N-methylamino)-2,4,6-triiodobenzenecarboxylate (40.00 g, 60.0 mmol) and sodium iodide (0.89 g, 6.0 mmol) in dry dimethylformamide (200 ml). After stirring at 50° C. for 24 hours the solvent was removed at reduced pressure. The residue was dissolved in chloroform (120 ml) and washed four times with a saturated sodium hydrogen carbonate solution and twice with water. After drying with magnesium sulfate, treatment with activated charcoal and filtration, the title compound was crystallised by concentrating the solution at reduced pressure. Yield: (79%). Purity by HPLC: 99%. $^1$H-NMR (DMSO-d$_6$): delta=1.25 (t, J=7 Hz, CH$_3$); 1.64 (d, J=6 Hz, CH$_3$); 1.67 (s, N(Me)COCH$_3$); 2.05 (s, NCOCH$_3$); 2.96 (s, NCH$_3$); 4.21 (q, J=7 Hz, CH$_2$); 6.97 (q, J=6 Hz, CH); 10.10 ppm (s, NH).

EXAMPLE 2

1-(Ethyloxycarbonyloxy)ethyl 5-(N-acetylamino)-3-(N-methylaminocarbonyl)-2,4,6-triiodobenzenecarboxylate 1-Chloroethyl ethyl carbonate (1.67 g, 11.0 mmol) was added dropwise at room temperature to a solution of potassium 5-(N-acetylamino)-3-(N-methylaminocarbonyl)-2,4,6-triiodobenzenecarboxylate (6.52 g, 10.0 mmol) and sodium iodide (150 mg, 1.0 mmol) in dry DMF (50 ml). After stirring at 50° C. for 24 hours the solvent was removed at reduced pressure. The residue was dissolved in chloroform and washed four times with a saturated sodium hydrogen carbonate solution and twice with water. After drying with magnesium sulfate and filtration, the solvent was removed at reduced pressure to give the title compound. Yield: (2.2 g, 38 %). Purity by HPLC: 98%. $^1$H-NMR (DMSO-d$_6$): delta=1.24 ( t, J=7 Hz, CH$_3$ ); 1.63 (d, J=6 Hz, CH$_3$); 2.03 (s, CH$_3$CO); 2.75 (d, J=3 Hz, NCH$_3$); 4.21 (q, J=7 Hz, CH$_2$): 6.93 (q, J=6 Hz, CH); 8.4–8.7 (m, NHMe); 10.03 ppm (s, NHAc).

EXAMPLE 3

1-(Ethyloxycarbonyloxy) ethyl 3-(alpha-(3-(N-acetyl-N-methylamino)-5-(methylaminocarbonyl)-2,4,6-triiodobenzoylamino)-acetylamine)-5-(N-(2-hydroxyethyl) aminocarbonyl)-2,4,6-triiodo-benzenecarboxylate 1-Chloroethyl ethyl carbonate (0.84 g, 5.5 mmol) was added dropwise at room temperature to a solution of cesium 3-(alpha-(3-(N-acetyl-N-methylamino)-5-(methylaminocarbonyl)-2,4,6-triiodoben- zoylamino)acetylamine)-5-(N-2-hydroxyethyl-)aminocarbonyl)-2,4,6-triiodo-benzenecarboxylate (7.00 g, 5.0 mmol) and sodium iodide (75 mg, 0.5 mmol) in dry DMF (25ml). After stirring at 50° C. for 24 hours the solvent was removed at reduced pressure. The residue was triturated, washed and filtered repeatedly, first with CHCl$_3$ and finally with H$_2$O, to give the title compound. Yield: (5.7 g, 82%). Both $^1$H- and $^{13}$C-NMR are similar for the title compound and the starting material (as free carboxylic acid) except for the carboxylic acid itself which is esterified in the title compound. $^1$H-NMR (DMSO-d$_6$) of the 1-ethyloxycarbonyloxyethyl group of the title compound is: delta=1.24 (t, J=7 Hz, CH$_3$); 1.63 (d, J=6 Hz, CH$_3$); 4.21 (q, J=7 Hz, CH$_2$); 6.94 ppm (q, J=6 Hz, CH). These chemical shifts are in accordance with the title compounds of Examples 1 and 2, and not with 1-chloroethyl ethyl carbonate which is the starting material (delta=1.24 (t, J=7 Hz, CH$_3$); 1.76 (d, J=6 Hz, CH$_3$); 4.21 (q, J=7 Hz, CH$_2$) 6.51 ppm (q, J=6 Hz, CH)).

EXAMPLE 4

1,3-Dioxolan-2-one-4-yl-5-(N-acetylamino)-3-(N-acetyl-N-methylamino)-2,4,6-triiodobenzenecarboxylate 4-Chloro-1,3-dioxolan-2-one (1.35 g, 11 mmol) was added at room temperature to a solution of potassium 5-(N-acetylamino)-3-(N-acetyl-N-methylamino)-2,4,6-triiodobenzenecarboxylate (6.66 g, 10 mmol) and sodium iodide (0.15 g, 1 mmol) in dry DMF (50 ml). After stirring at 50° C. for 6 hours and at room temperature for 4 days the solvent was removed at reduced pressure. The residue was dissolved in chloroform (100 ml) and washed four times with a saturated sodium hydrogen carbonate solution and finally twice with water. After treatment with magnesium sulfate the solution was finally evaporated to dryness. Yield: 5.6 g. Purity by HPLC: 93%. $^1$H-NMR (DMSO-d$_6$): delta=1.67 (N(CH$_3$)COCH$_3$); 2.05(NCOCH$_3$); 2.96(NCH$_3$); 4.7; 4.9(CH$_2$); 7.02(CH); 10.14 ppm(NH).

EXAMPLE 5

1-(Phenyloxycarbonyloxy)ethyl 5-(N-acetylamino)-3-(N-acetyl-N-methylamino)-2,4,6-triiodobenzenecarboxylate 1-Chloroethyl phenyl carbonate (prepared according to Synthesis 1986, 627) (2.21 g, 11 mmol) was added at room temperature to a solution of potassium 5-(N-acetylamino)-3-(N-acetyl-N-methylamino)-2,4,6-triiodobenzenecarboxylate (6.66 g, 10 mmol) and potassium iodide (0.17 g, 1 mmol) in dry DMF. After stirring at 50° C. for 6 hours and at room temperature for 4 days the solvent was removed at reduced pressure. The residue was suspended in chloroform (100 ml) and washed four times with a saturated sodium hydrogen carbonate solution and twice with water. After drying with magnesium sulfate the solution was evaporated to dryness. Yield: 7.3 g. Purity by HPLC: 98%. $^1$H-NMR (DMSO-d$_6$): delta=1.68 (N(CH$_3$)COCH$_3$); 1.74 (CHCH$_3$); 2.05 (NCOCH$_3$); 2.97 (NCH$_3$); 7.05 (CH); 7.25–7.52 (arom.); 10.14 ppm (NH).

EXAMPLE 6

1-(Benzyloxycarbonyloxy)ethyl 5-(N-acetylamino)-3-(N-acetyl-N-methylamino)-2,4,6-triiodobenzenecarboxylate 1-Chloroethyl benzyl carbonate (prepared according to Synthesis 1986, 627), (2.36 g, 11.0 mmol) was added at room temperature to a solution of potassium 5-(N-acetylamino)-3-(N-acetyl-N-methylamino)-2,4,6-triiodobenzenecarboxylate (6.66 g, 20 mmol) and sodium iodide (0.15 g, 1 mmol) in dry DMF (50 ml). After stirring at 50° C. for 7 hours and at room temperature for 7 days the solvent was removed at reduced pressure. The residue was dissolved in chloroform (100 ml) and washed four times with a saturated sodium hydrogen carbonate solution and twice with water. After treatment with magnesium sulfate the solution was evaporated to dryness. Yield: 6.8 g. Purity by HPLC: 97% $^1$H-NMR(DMSO-d$_6$): delta=1.64 (CHC$\underline{H_3}$); 1.66(N(CH$_3$)COC$\underline{H_3}$); 2.05 (NCOC$\underline{H_3}$); 5.23 ($\overline{CH_2}$); 7.00 (CH); 7.30–7.45(arom.); 10.12 ppm (NH).

EXAMPLE 7

1-(Thenyloxycarbonyloxy)ethyl 5-(N-acetylamino)-3-(N-acetyl-N-methylamino)-2,4,6-triiodobenzenecarboxylate i) 1-Chloroethyl thenylcarbonate:

1-Chloroethyl chloroformate (28.6 g, 0.2 mol) and 2-hydroxymethyl-thiophene (20.6 g, 0.18 mol) were dissolved in chloroform (220 ml) at 0° C. Pyridine (15.8 g, 0.2 mol) was added dropwise during 35 minutes maintaining the temperature below 10° C. After stirring at room temperature for 24 hours the precipitate was filtered off. The organic phase was washed three times with 1 normal hydrochloric acid, once with a saturated sodium hydrogen carbonate solution and finally twice with water. The organic solution was dried with magnesium sulfate and the solvent was removed at reduced pressure. The residue was distilled in vacuo. Yield: 36.5 g. $^1$H-NMR (DMSO-d$_6$): delta=1.76 (CH$_3$); 5.41 (CH$_2$); 6.53 (C$\underline{H}$CH$_3$); 7.04, 7.25; 7.59 ppm (thiophene).

ii) 1-(Thenyloxycarbonyloxy)ethyl 5-(N-acetylamino)-3-(N-acetyl-N-methylamino)-2,4,6-triiodobenzene carboxylate:

1-Chloroethyl thenyl carbonate (2.43 g, 11 mmol) was added at room temperature to a solution of potassium 5-(N-acetylamino)-3-(N-acetyl-N-methylamino)-2,4,6-triiodobenzenecarboxylate (6.66 g, 10 mmol) and potassium iodide (0.17 g, 1 mmol) in dry DMF. After stirring at 50° C. for 5 hours and at room temperature for 4 days the solvent was removed at reduced pressure. The residue was suspended in chloroform (100 ml) and washed three times with a saturated sodium hydrogen carbonate solution and finally twice with water. After drying with magnesium sulfate the solution was evaporated to dryness. Yield: 7.9 g. Purity by HPLC: 88%. $^1$H-NMR (DMSO-d$_6$): delta=1.64 (CHC$\underline{H_3}$); 1.65 (N(CH$_3$)COCH$_3$); 2.05 (NCOCH$_3$ ); 2.95 (N$\overline{CH_3}$); 5.41 (CH$_2$); 7.00 ($\overline{CH}$CH$_3$); 7.05; 7.25; 7.61 (thiophene); 10.11 ppm (NH).

EXAMPLE 8

1-(2-Methoxyethyloxycarbonyloxy)ethyl 5-(N-acetylamino)-3-(N-acetyl-N-methylamino)-2,4,6-triiodobenzenecarboxylate i) 1-Chloroethyl 2-methoxyethane carbonate:

1-Chloroethyl chloroformate (28.6 g, 0.2 mol) and 2-methoxyethanol (13.7 g, 0.18 mol) were dissolved in chloroform (220 ml) at 0° C. Pyridine (15.8 g, 0.2 mol) was added dropwise during 45 minutes maintaining the temperature below 12° C. After stirring at room temperature for 2 hours the mixture was washed three times with 1 normal hydrochloric acid, once with a saturated sodium hydrogen carbonate solution and finally twice with water. The organic phase was dried with magnesium sulfate and the solvent was removed at reduced pressure. The residue was distilled in vacuo. Yield: 75%. $^1$H-NMR: delta=1.76 (CHC$\underline{H_3}$); 3.27 (OCH$_3$); 3.55 (C$\underline{H_2}$OCH$_3$); 4.27 (COOCH$_2$); 6.51 (CH).

ii) 1-(2-Methoxyethyloxycarbonyloxy)ethyl 5-(N-acetylamino)-3-(N-acetyl-N-methylamino)-2,4,6-triiodobenzenecarboxylate:

1-Chloroethyl 2-methoxyethane carbonate (2.0 g, 11 mmol) was added at room temperature to a solution of potassium 5-(N-acetylamino)-3-(N-acetyl-N-methylamino)-2,4,6-triiodobenzenecarboxylate (6.66 g, 10 mmol) and potassium iodide (0.17 g, 1 mmol) in dry DMF. After stirring at 50° C. for 4 hours and at room temperature for 3 days the solvent was removed at reduced pressure. The residue was suspended in chloroform (100 ml) and washed three times with a saturated sodium hydrogen carbonate solution and finally twice with water. After drying with magnesium sulfate the solution was evaporated to dryness. Yield: 7.1 g. Purity by HPLC: 79%. $^1$H-NMR (DMSO-d$_6$): delta=1.65 (CHC$\underline{H_3}$); 1.66 (N(CH$_3$)COCH$_3$); 2.05 (NCOCH$_3$); 2.96 (NC$\underline{H_3}$); 3.26 (OCH$_3$); 3.55 (CH$_2$OC$\underline{H_3}$); 4.29 (COOCH$_2$); 6.98 (CH); 10.12 ppm (NH). FAB-MS: M+1=775.

EXAMPLE 9

1-(2-[N-(3,5-bis-((2,2-dimethyl-1,3-dioxolan-4-yl)-methylaminocarbonyl)-2,4,6-triiodophenyl)-acetylamino]ethyloxycarbonyloxy)ethyl 5-(N-acetylamino)-3-(N-acetyl-N-methylamino)-2,4,6-triiodobenzenecarboxylate (i) 1-Chloroethyl 2-(N-(3,5-bis-((2,2-dimethyl-1,3-dioxolan-4-yl )-methylaminocarbonyl)-2,4,6-triiodophenyl)acetylamino)ethyl carbonate:

1-Chloroethyl chloroformate (0.77 g, 5.5 mmol) and 5-(N-acetyl-N-(2-hydroxyethyl)amino)-N,N'-bis( (2,2-dimethyl-1, 3-dioxolan-4-yl)-methyl) 2,4,6-triiodo-1,3-benzenedicarboxamide (4.36 g, 5 mmol) were dissolved in dichloromethane (10 ml) at 0° C. Pyridine (4.35 mg, 5.5 mmol) was added during 45 min. After stirring at 0° C. for one hour 1-chloroethyl chloroformate (0.77 g, 5.5 mmol) and pyridine (4.35 mg, 5.5 mmol) were added once more. After three days at room temperature the mixture was washed four times with 0.1 normal hydrochloric acid, twice with a saturated sodium hydrogen carbonate solution and finally once with water. The organic phase was dried with magnesium sulfate and the solvent was evaporated under reduced pressure. Yield 3.8 g.

ii) 1-(2-[N-(3,5-bis-((2,2-dimethyl-1,3-dioxolan-4-yl)-methylaminocarbonyl)-2,4,6-triiodophenyl)acetylamino)]ethyloxycarbonyloxy)ethyl 5-(N-acetylamino)-3-(N-acetyl-N-methylamino)-2,4,6 -triiodobenzenecarboxylate:

1-Chloroethyl 2-(N-(3,5-bis-((2,2-dimethyl-1,3-dioxolan-4-yl)-methylaminocarbonyl)-2,4,6-triiodophenyl)acetylamino)ethyl carbonate (3.1 g, 3.3 mmol) was added at room temperature to a solution of potassium 5-(N-acetylamino)-3-(N-acetyl-N-methylamino)-2,4,6-triiodobenzenecarboxylate (2.00 g, 3 mmol) and potassium iodide (50 rag, 0.3 mmol) in dry DMF. After stirring at 50° C. for 18 hours and at room temperature for one day the solvent was removed at reduced pressure. The residue was suspended in chloroform (50 ml) and DMF (5 ml) and washed twice with a sodium hydrogen carbonate solution and twice with water. After treatment of the organic phase with magnesium sulfate and charcoal the solution was evaporated to dryness. Yield: 2.65 g. FAB-MS: M+1=1528.

EXAMPLE 10

1-(2-(N-(3,5-bis (
(2,3-dihydroxypropyl)-aminocarbonyl)-2,4,6-triiodophenyl)-acetylamino)-ethyloxycarbonyloxy) ethyl 5-(N-acetylamino)-3-(N-acetyl-N-methylamino)-2,4,6-triiodobenzenecarboxylate 1-(2-[N-(3,5-bis((2,2-dimethyl-1,3-dioxolan-4-yl)methylaminocarbonyl)-2,4,6 -triiodophenyl)-acetylamino]ethyloxycarbonyloxy)ethyl 5-(N-acetylamino)-3-(N-acetyl-N-methylamino)-2,4,6-triiodobenzenecarboxylate (0.5 g, 0.3 mmol) was dissolved in DMF (3.5 ml) and water (1.5 ml). 1N hydrochloric acid (0.6 ml, 0.6 mmol) was added at room temperature. After stirring at 50° C. for 2 hours the solution was evaporated to dryness. Yield: 0.4 g. FAB/MS: 1490 (M+H+).

EXAMPLE 11

1-(Ethyloxycarbonyloxy)ethyl
3,5-di(acetylamino)-2,4,6-triiodobenzenecarboxylate 1-Chloroethyl ethyl carbonate (1.68 g, 11.0 mmol) was added at room temperature to a solution of potassium 3,5-di (acetylamino)-2,4,6-triiodobenzenecarboxylate (6.52 g, 10.0 mmol) and sodium iodide (0.30 g, 2.0 mmol) in dry DMF (100 ml). After stirring at 60° C. for 2 hours and at 40° C. for 65 hours the solvent was removed at reduced pressure. The residue was suspended in chloroform (100 and washed four times with a saturated sodium hydrogen carbonate solution and finally twice with water. After drying with magnesium sulfate the solution was evaporated to dryness. Yield: 2.45 g Purity by HPLC: 98.5% $^1$H-NMR(DMSO-d$_6$): delta=1.24(CH$_2$CH$_3$); 1.63(CHCH$_3$); 2.02(COCH$_3$); 4.20(CH$_2$CH$_3$); 6.93(CHCH$_3$); 10.03 ppm (NH). FAB/MS: 731 (M+H+)

EXAMPLE 12

Phenyloxycarbonyloxymethyl
5-(N-acetylamino)-3-(N-acetyl-N-methylamino)-2,4,6-triiodobenzenecarboxylate (i) Chloromethyl phenyl carbonate:
Phenyl chloroformate (9.0 g, 57.5 mmol) was dissolved in 1,2-dichloroethane (50 ml) and pyridine (0.22 g, 2.8 mmol) was added dropwise to the stirred solution. In another reactor, paraformaldehyde (7.0 g, 233.1 mmol) was heated with a heat gun to generate the gaseous monomer. The formaldehyde gas was bubbled into the first reactor through a tube with the outlet below the surface of the liquid. Stirred at 65° C. for 3 hours. Washed three times with water, dried (MgSO$_4$) and concentrated. Distillation (Bp. 64°–67° C., 5×10$^{-4}$ mbar) yielded 2.7 g product. The product was further purified by flash chromatography (Silikagel 60, petroleum ether/ethyl acetate 95:5). Yield: 2.1 g. $^1$H-NMR (CDCl$_3$): delta=5.78 (CH$_2$); 7.18–7.41 ppm (phenyl).

ii) Phenyloxycarbonyylmethyl 5-(N-acetylamino)-3-(N-acetyl-N-methylamino)-2,4,6-triiodobenzenecarboxylate:

Chloromethyl phenyl carbonate (0.50 g, 2.7 mmol) was added at room temperature to a solution of potassium 5-(N-acetylamino)-3-(N-acetyl-N-methylamino)-2,4,6-triiodobenzenecarboxylate (1.62 g, 2.4 mmol) and sodium iodide (0.038 g, 0.25 mmol) in dry DMF (15 ml). After stirring at 50° C. for 5 hours and at room temperature for 18 hours the solvent was removed at reduced pressure. The residue was suspended in chloroform (25 ml) and washed four times with a saturated sodium hydrogen carbonate solution and finally twice with water. After drying with magnesium sulfate the solution was evaporated to dryness. Yield: 0.67 g Purity by HPLC: 99.2% $^1$H-NMR(DMSO-d$_6$): delta=1.68 (NCH$_3$COCH$_3$); 2.06 (NHCOCH$_3$); 2.97 (NCH$_3$); 6.08 (CH$_2$); 7.28–7.49 (phenyl); 10.14 ppm (NH). FAB/MS: 779 ((M+H)+).

EXAMPLE 13

1-(Phenyloxycarbonyloxy)-3-phenylpropyl
5-(N-acetylamino)-3-(N-acetyl-N-methylamino)-2,4,6-triiodobenzenecarboxylate i) 1-Chloro-3-phenylpropyl phenyl carbonate:
Phenyl chloroformate (0.80 g, 5.1 mmol) and 3-phenylpropionaldehyde (0.96 g, 7.2 mmol) were dissolved in 1,2-dichloroethane (5 ml) and pyridine (0.020 g, 0.25 mmol) was added dropwise to the stirred solution. Stirred at 80° C. for 2 days. Washed with water (10 ml), dried (MgSO$_4$) and concentrated. Purified by flash chromatography (Silikagel 60, petroleum ether/ethyl acetate 95:5). Yield: 0.45 g $^1$H-NMR (CDCl$_3$): delta=2.43 (CH$_2$CH); 2.87 (CH$_2$CH$_2$CH); 6.34 (CH); 7.19–7.41 ppm (phenyl).

ii) 1-(Phenyloxycarbonyloxy)-3-phenylpropyl 5-(N-acetylamino)-3-(N-acetyl-N-methylamino)-2,4,6-triiodobenzenecarboxylate 1-Chloro-3-phenylpropyl phenyl carbonate (0.30 g, 1.03 mmol) was added at room temperature to a solution of potassium 5-(N-acetylamino)-3-(N-acetyl-N-methyl-amino)-2,4,6-triiodobenzenecarboxylate (0.62 g, 0.93 mmol) and sodium iodide (0.014 g, 0.093 mmol) in dry DMF (5 ml). After stirring at 50° C. for 5 hours and at room temperature for 2 days the solvent was removed at reduced pressure. The residue was suspended in chloroform (15 ml) and washed four times with a saturated sodium hydrogen carbonate solution and finally twice with water. After drying with magnesium sulfate the solution was evaporated to dryness. Yield: 0.26 g. Purity by HPLC: 94.4% $^1$H-NMR (DMSO-d$_6$): delta=1.68 (NCH$_3$COCH$_3$); 2.06 (NHCOCH$_3$); 2.38 (CH$_2$CH); 2.83 (CH$_2$CH$_2$CH); 2.98 (NCH$_3$); 7.02 (CH); 7.19–7.52 (phenyl); 10.15 ppm (NH). FAB/MS: 883 ((M+H+).

EXAMPLE 14

1-(Phenyloxycarbonyloxy)pentyl
5-(N-acetylamino)-3-(N-acetyl-N-methylamino)-2,4,6-triiodobenzenecarboxylate i) 1-Chloropentyl phenyl carbonate:
Phenyl chloroformate (2.0 g, 12.8 mmol) and n-valeraldehyde (1.3 g, 15.1 mmol) were dissolved in 1,2-dichloroethane (10 ml) and pyridine (0.06 g, 0.76 mmol) was added dropwise to the stirred solution.

Stirred at 80° C. for 1 day. Washed with water (10 ml), dried (MgSO$_4$) and concentrated. Purified by flash chromatography (Silikagel 60, petroleum ether/ethyl acetate 95:5). Yield: 0.26 g GC/MS: 242.0 (M+).

ii) 1-(Phenyloxycarbonyloxy)pentyl 5-(N-acetylamino)-3-(N-acetyl-N-methylamino)-2,4,6-triiodobenzenecarboxylate:

1-Chloropentyl phenyl carbonate (0.14 g, 0.58 mmol) was added at room temperature to a solution of potassium 5-(N-acetylamino)-3-(N-acetyl-N-methylamino)-2,4,6-triiodobenzenecarboxylate (0.35 g, 0.53 mmol) and sodium iodide (0,008 g, 0.053 mmol) in dry DMF (3 ml). After stirring at 50° C. for 5 hours and at room temperature for 2 days the solvent was removed at reduced pressure. The residue was suspended in chloroform (15 ml) and washed four times with a saturated sodium hydrogen carbonate solution and finally twice with water. After drying with magnesium sulfate the solution was evaporated to dryness. Yield: 0.04 g. Purity by HPLC: 94.8% $^1$H-NMR (DMSO-d$_6$): delta=0.92(CH$_3$CH$_2$); 1.31–1.55 (CH$_3$CH$_2$CH$_2$); 1.68 (NCH$_3$COCH$_3$); 2.04 (CH$_2$CH); 2.05 (NHCOCH$_3$); 2.97 (NCH$_3$); 6.95 (CH); 7.27–7.49 (phenyl); 10.13 ppm (NH). FAB/MS: 835 ((M+H)+).

EXAMPLE 15

1-(Phenyloxycarbonyloxy)-1-phenylmethyl 5-(N-acetylamino)-3-(N-acetyl-N-methylamino)-2,4,6-triiodobenzenecarboxylate i) 1-Chloro-1-phenylmethyl phenyl carbonate:

Phenyl chloroformate (3.0 g, 19.2 mmol) and benzaldehyde (2.4 g, 23.0 mmol) were dissolved in 1,2-dichloroethane (15 ml) and pyridine (0.09 g, 1.14 mmol) was added dropwise to the stirred solution. Stirred at 80° C. for two days and at 100° C. for one day. Washed with water (25 ml ), the aqueous phase was back-extracted with di chloromethane (25 ml). The combined organic phases were dried (MgSO$_4$) and concentrated. Purified by flash chromatography (Silikagel 60, petroleum ether/ethyl acetate 95:5 ). Yield: 1.5 g. $^1$H-NMR (CDCl$_3$): delta=7.34 (CH); 7.20–7.61 ppm (phenyl). GC/MS: 262.1 (M+).

ii) 1-(Phenyloxycarbonyloxy)-1-phenylmethyl 5-(N-acetylamino)-3-(N-acetyl-N-methylamino)-2,4,6-triiodobenzenecarboxylate:

1-Chloro-1-phenylmethyl phenyl carbonate (0.63 g, 2.4 mmol) was added at room temperature to a solution of potassium 5-(N-acetylamino)-3-(N-acetyl-N-methylamino)-2,4,6-triiodobenzene carboxylate (1.44 g, 2.2 mmol) and sodium iodide (0.034 g, 0.23 mmol) in dry DMF (12 ml). After stir ring at 60° C. for 2 hours and at room temperature for 18 hours the solvent was removed at reduced pressure. The residue was suspended in chloroform (20 ml) and washed four times with a saturated sodium hydrogen carbonate solution and finally twice with water. After drying with magnesium sulfate the solution was evaporated to dryness. Yield: 0.90 g. Purity by HPLC: 96.6% $^1$H-NMR(DMSO-d$_6$): delta=1.67 (NCH$_3$COCH$_3$ ); 2.05 (NHCOCH$_3$); 2.96 (NCH$_3$); 7.29–7.54 (phenyl); 7.71 (CH); 10.13 ppm (NH). FAB/MS: 854 (M+).

EXAMPLE 16

1-(Hexyloxycarbonyloxy)ethyl 5-(N-acetylamino)-3-(N-acetyl-N-methylamino)-2,4,6-triiodobenzenecarboxylate i) 1-Chloroethyl hexylcarbonate:

1-Chloroethyl chloroformate (10.0 g, 69.9 mmol) and 1-hexanol (6.5 g, 63.6 mmol) were dissolved in chloroform (80 ml) at 0° C. Pyridine (5.5 g, 69.5 mmol) was added dropwise during 17 minutes maintaining the temperature below 10° C. After stirring at room temperature for 20 hours the organic phase was washed three times with 1 normal hydrochloric acid, once with a saturated sodium hydrogen carbonate solution and finally twice with water. The organic solution was dried with magnesium sulfate and the solvent was removed at reduced pressure. The residue (11 .6 g) was distilled in vacuo (Bp. 61°–72° C., 3×10$^{-3}$ mbar). Yield: 9.0 g. $^1$H-NMR (CDCl$_3$): delta=0.89 (CH$_2$CH$_3$); 1.28–1.40 (CH$_2$CH$_2$CH$_2$CH$_3$); 1.69 (OCH$_2$CH$_2$); 1.83 (CH$_3$CH); 4.20 (OCH$_2$); 6.43 ppm (CH).

ii) 1-(Hexyloxycarbonyloxy)ethyl 5-(N-acetylamino)-3-(N-acetyl-N-methylamino)-2,4,6-triiodobenzenecarboxylate:

1-Chloroethyl hexylcarbonate (0.47 g, 2.3 mmol) was added at room temperature to a solution of potassium 5-(N-acetylamino)-3-(N-acetyl-N-methylamino)-2,4,6-triiodobenzenecarboxylate (1.51 g, 2.3 mmol) and sodium iodide (0,036 g, 0.24 mmol) in dry DMF (12 ml). After stirring at 60° C. for 3 hours and at room temperature for 18 hours the solvent was removed at reduced pressure. The residue was suspended in chloroform (20 ml) and washed three times with a saturated sodium hydrogen carbonate solution and finally twice with water. After drying with magnesium sulfate the solution was evaporated to dryness. Yield: 0.88 g, Purity by HPLC: 95.2% $^1$H-NMR (DMSO-d$_6$); delta=0.86 (CH$_2$CH$_3$); 1.22–1.36 (CH$_2$CH$_2$CH$_2$CH$_3$); 1.62 (OCH$_2$CH$_2$); 1.64 (CHCH$_3$); 1.66 (NCH$_3$COCH$_3$); 2.04 (NHCOCH$_3$); 2.95 (NCH$_3$); 4.16 (OCH$_2$); 6.96 (CH); 10.11 ppm (NH). FAB/MS: 801 ((M+H)+).

Particle Preparation 1

Bovine serum albumin, BSA, (0.75 g) was dissolved in distilled water (25.0 ml) and filtered through a membrane filter with pore size 0.45 micron. A filtered solution (0.22 micron) of the product of Example 1 (0.2 g) in 96% ethanol (5.0ml) was slowly added to the BSA solution under vigorous stirring over a prolonged period of time. The microparticles formed were centrifuged and washed repeatedly. The size and size-distribution of the particles were analysed by Coulter Multisizer and light- and electron microscopy. The mean diameter was 2.0 microns, which was also the diameter of the main fraction.

Particle Preparation 2

Bovine serum albumin, BSA, (0.75 g) was dissolved in distilled water (25.0 ml) and filtered through a membrane filter with pore size 0.45 micron. A filtered solution (0.22 micron) of the product of Example 1 (0.2 g) in 96% ethanol (5.0 ml) was slowly added to the BSA solution under vigorous ultrasonic stirring over a prolonged period of time. The microparticles formed were centrifuged and washed repeatedly. The size and size-distribution of the particles were analysed by Coulter Multisizer and light microscopy. The mean diameter was 2.0 microns, which was also the diameter of the main fraction.

Particle Preparation 3

A solution containing 2% polysorbat 80 (Tween 80) in distilled water was prepared (25.0 ml) and filtered through a membrane filter (0.45 micron).

A filtered solution (0.22 micron) of the product of Example 1 (0.2 g) in 96% ethanol (5.0 ml) was slowly added to the Tween 80 solution under vigorous stirring.

The microparticles formed were centrifuged and washed repeatedly before reconstitution in sterile phosphate buffered saline (1.8 ml) containing 0.25% Tween 80.

The size and size distribution of the particles were analyzed by Coulter Counter and light microscopy. The mean diameter by volume was 2 microns.

Particle Preparation 4

A 3% solution of human serum albumin (HSA) in distilled water was prepared (150 ml) and filtered through a membrane filter (0.45 micron). A filtered solution (0.22 micron) of the product of Example 1 (1.2 g) in 96% ethanol (30.0 ml) was slowly added to the HSA solution under vigorous stirring.

The microparticles formed were centrifuged and washed repeatedly before reconstitution in sterile phosphate buffered saline (10.7 ml). The size and size distribution of the particles were analyzed by Coulter Counter and light microscopy.

The mean diameter by volume was 2.5–3.5 microns.

Particle Preparation 5

A 0.4% solution of human serum albumin (HSA) in distilled water was prepared (60.0 ml) and filtered through a membrane filter (0.45 microns). A filtered solution (0.22 micron) of the product of Example 1 (0.6 g) in 96% ethanol (15.0 ml) was slowly added to the HSA solution under vigorous homogenizing.

The microparticles formed were centrifuged and washed repeatedly before reconstitution in sterile phosphate buffered saline (5.3 ml) containing 0.4% HSA.

The size and size distribution of the particles were analyzed by Malvern Mastersizer and light microscopy.

The mean diameter by volume was 1.45 microns.

Particle Preparation 6

A solution containing 0.4% human serum albumin (HSA) and 2% propylene glycol in distilled water was prepared (60.0 ml) and filtered through a membrane filter (0.45 micron).

A filtered solution (0.22 micron) of the product of Example 1 (0.6 g) in 96% ethanol (15.0 ml) was slowly added to the HSA/propylene glycol solution under vigorous homogenizing.

The microparticles formed were centrifuged and washed repeatedly before reconstitution in sterile phosphate buffered saline (5.3 ml) containing 0.2% propylene glycol.

The size and size distribution of the particles were analyzed by Malvern Mastersizer and light microscopy.

The mean diameter by volume was 1.5–1.7 microns.

Pharmaceutical Formulation 1

The particles of Particle Preparation 1 (1.0 g) were dispersed in a sterile filtered isotonic 0.9% sodium chloride/water for injection solution (100 ml) under vigorous stirring until a homogeneous suspension was achieved.

Pharmaceutical Formulation 2

The particles of Particle Preparation 1 (1.0 g) were suspended in a sterile filtered 0.9% sodium chloride/water for injection solution (100 ml) containing bovine serum albumin (3.0 g) under vigorous stirring until a homogeneous suspension was achieved.

Pharmaceutical Formulation 3

The particles of Particle Preparation 1 (1.0 g) were suspended in a sterile phosphate buffered saline solution (100 ml) until a homogeneous suspension was achieved.

Pharmaceutical Formulation 4

The particles of Particle Preparation 1 (2.8 g) were suspended in a sterile phosphate buffered saline solution (100 ml) until a homogeneous suspension was achieved.

In Vitro Biodegradation

The powdered product of Example 1 was suspended in Seronorm (0.5 mg/ml) at pH 7.4 and agitated at 37° C. As a control the experiment was also performed in phosphate buffered saline (PBS) at pH 7.4.

At different time points samples were taken from the supernatant after centrifugation of the vial (4000 rpm, 10 min). The release of Isopaque (5-(N-acetylamino)-3-(N-acetyl-N-methylamino)-2,4,6-triiodobenzene carboxylic acid) was analysed by HPLC. After 6 hours 100% of the substance was hydrolysed. In PBS only 1.1% was hydrolysed during the same period.

In Vivo Metabolism

The particles of Pharmaceutical Formulation 3 were injected intravenously into the tail veins of rats. The dose was 200 mg/kg, injection rate 1 ml/min and concentration 10 mg/ml. 15 min after injection about 70% of the dose was found in the liver. This uptake gave 1.4 mg I/g liver. The iodine content was stable up to 3 hours p.i., and then decreased to 24% after 6 hours. 24 hours p.i. only 4% was left in the liver. Bile and urine were sampled during the first 3 hours after injection. Excretion through these routes was 8.1 and 3.4 of the injected dose respectively. All iodine was excreted as Isopaque (5-(N-acetylamino)-3-(N-acetyl-N-methylamino)-2,4,6-triiodobenzenecarboxylic acid). During a 72 hour period all iodine was excreted via the urine or faeces in equal amounts (about 50% through each). To assess embolization of particles in the lung capillaries iodine content in this organ was measured. Only 1.3% of the injected dose was found in the lungs 15 min after injection, and iodine could not be detected in the lungs 24 hours later. This shows that the pulmonary trapping was minimal.

CT Studies in rabbit

Contrast enhancement in the liver was investigated in rabbits. Anaesthetized animals were placed in a Siemens CT scanner and injected with particles of Pharmaceutical Formulation 4 in the marginal ear vein. Particle concentration was 28 mg/ml. A particle dose corresponding to 75 mg I/kg gave an increase in liver contrast from a basal level of 75 HU to about 120 HU. Thus, the contrast enhancement on this dose level was about 35–40 HU. This contrast enhancement was stable during the observation period of 15 minutes. The average iodine content in these livers was 1.1 mg I/g liver. These results were compared to dynamic CT in other rabbits which were injected with iohexol (350 mg I/ml). About 8 times more iodine had to be injected in these animals to achieve the same contrast enhancement of the liver. With this vascular contrast medium, the enhancement was transient, lasting for one or two minutes.

We claim:
1. A water-insoluble iodinated ester of formula (I):

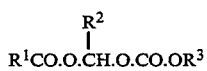

in which
- $R^1$ is a substituted or unsubstituted $C_{1-20}$ aliphatic, $C_{7-20}$ araliphatic or $C_{6-20}$ aryl group;
- $R^2$ is hydrogen or a substituted or unsubstituted $C_{1-6}$ aliphatic, $C_{6-10}$ aryl or $C_{7-20}$ araliphatic group;
- $R^3$ is a substituted or unsubstituted $C_{1-20}$ aliphatic, $C_{7-20}$ araliphatic or $C_{6-20}$ aryl group or a 5- to 6-membered heterocyclic group having one or more heteroatoms selected from O, S and N;
- or $R^2$ and $R^3$ together represent a substituted or unsubstituted $C_{1-4}$ alkylene group;
- or $R^3$ represents a substituted or unsubstituted triiodophenyl group linked to the oxygen atom via a bridging N-alkylamino, N-alkylcarbamoyl or N-acylamino group which bridging group may carry an additional hydroxy group;
- and wherein the substituents in the groups $R^1$ to $R^3$ are one or more hydroxyl, $C_{1-5}$ alkoxy, $C_{1-6}$ acyloxy, $C_{1-5}$ alkylthio, N—$C_{1-6}$-alkylamino, N—$C_{1-6}$ acylamino, N—$C_{1-6}$-acyl-N—$C_{1-6}$-alkylamino, carbamoyl or N—$C_{1-6}$-alkylcarbamoyl groups or halogen atoms,
- wherein any N-acyl or N-alkyl group may in turn be substituted by one or more hydroxy, $C_{1-5}$ alkoxy or $C_{1-6}$ acyloxy groups, and when any of $R^1$ to $R^3$ contains an aromatic ring said ring may additionally be substituted by one or more $C_{1-6}$ alkyl groups;
- the molecule containing at least one triiodophenyl group in $R^1$ and/or $R^3$, and being metabolisable to products which are soluble in body fluids and are physiologically acceptable.

2. 1-(Ethyloxycarbonyloxy)ethyl-3-($\alpha$-(3-(N-acetyl-N-methylamino)-5-(methylaminocarbonyl)-2,4,6-triiodobenzoylamino)-acetylamino)-5-(N-(2-hydroxyethyl)aminocarbonyl)-2,4,6-triiodo-benzenecarboxylate.

3. 1-(Thenyloxycarbonyloxy)ethyl-5-(N-acetylamino)-3-(N-acetyl-N-methylamino)-2,4,6-triiodobenzenecarboxylate.

4. 1-(2-[N-(3,5-bis-((2,2-dimethyl-1,3-dioxolan-4-yl)-methylaminocarbonyl)-2,4,6-triiodophenyl)-acetylamino]ethyloxycarbonyloxy)ethyl-5-(N-acetylamino)-3-(N-acetyl-N-methylamino)-2,4,6-triiodobenzenecarboxylate.

5. 1-(2-(N-(3,5-bis-((2,3-dihydroxypropyl)-aminocarbonyl)-2,4,6-triiodophenyl)acetylamino)-ethyloxycarbonyloxy)ethyl-5-(N-acetylamino)-3-(N-acetyl-N-methylamino)-2,4,6-triiodobenzenecarboxylate.

* * * * *